(12) United States Patent
Nakajima et al.

(10) Patent No.: US 6,461,848 B1
(45) Date of Patent: Oct. 8, 2002

(54) HUMAN HEPARANASE POLYPEPTIDE AND CDNA

(75) Inventors: Motowo Nakajima, Hyogo; Minako Funakubo, Kanagawa, both of (JP)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/601,777

(22) PCT Filed: Feb. 5, 1999

(86) PCT No.: PCT/EP99/00777

§ 371 (c)(1),
(2), (4) Date: Aug. 7, 2000

(87) PCT Pub. No.: WO99/40207

PCT Pub. Date: Aug. 12, 1999

(30) Foreign Application Priority Data

Feb. 9, 1998 (GB) .............................. 9802725

(51) Int. Cl.⁷ ..................... C12P 21/06; C12N 9/00; C12N 9/24; C12N 9/42; C12N 1/20
(52) U.S. Cl. .................... 435/209; 435/69.1; 435/183; 435/200; 435/252.3; 435/320.1; 435/325; 424/94.61; 536/23.2
(58) Field of Search ..................... 435/183, 2, 252–3, 435/320.1, 69.1, 209, 325; 424/94.61; 536/23.2

(56) References Cited

U.S. PATENT DOCUMENTS 5,968,822 A * 10/1999 Pecker et al.
6,242,238 B1 * 6/2001 Freeman et al.

FOREIGN PATENT DOCUMENTS

| WO | 91 02977 A | 3/1991 |
| WO | 95 04158 A | 2/1995 |
| WO | 96 33726 A | 10/1996 |
| WO | 99 11798 A | 3/1999 |
| WO | 99 21975 A | 5/1999 |

OTHER PUBLICATIONS

Jin et al., "The molecular cloning and characterization of human heparanase cDNA and the immunochemical localization of heparanase in metastatic melanomas," Dissertation Abstracts International, Vol. 53(11), pp.5515B, Abstract XP002106139 (1993).

Jin L. et al., "Molecular cloning and expression of human heparanase cDNA," 83rd Annual Meeting of the American Association for Cancer Research, San Diego, CA, USA, May, 20–23, Abstract XP002106813 (1992).

Goshen et al., "Purification and characterization of placental heparanase and its expression by cultured cytotrophoblasts," Molecular Human Reproduction, Vol. 2(9), pp. 679–684, Abstract XP002106141 (1996).

Hillier et al., "The WashU–Merck EST Project Washington University (MO)," Jan. 6, 1996, Abstract XP002106145.

Strausberg, "Cancer Genome Anatomy Project, National Cancer Institute USA," Jun. 20, 1997, Abstract XP002106146.

* cited by examiner

Primary Examiner—Rebecca E. Prouty
Assistant Examiner—Manjunath N. Rao
(74) Attorney, Agent, or Firm—Diane Tso

(57) ABSTRACT

This invention relates to identified polynucleotides, polypeptides encoded by such polynucleotides, the use of such polynucleotides and polypeptides, as well as the production of such polynucleotides and polypeptides. More particularly, a polypeptide of the present invention is "heparanase" obtainable from the human SV40-transformed fibroblast cell line ATCC CCL 75.1. The heparanase is an endoglucuronidase capable of specifically degrading heparan sulfate into 6 to 20 kDa fragments.

11 Claims, No Drawings

SEQUENCE LISTING

<160> NUMBER OF SEQ ID NOS: 2

<210> SEQ ID NO 1
<211> LENGTH: 3726
<212> TYPE: DNA
<213> ORGANISM: Human

<400> SEQUENCE: 1

```
cagcgctgct ccccgggcgc tcctcccgg gcgctcctcc ccaggcctcc cgggcgcttg      60
gatcccggcc atctccgcac ccttcaagtg ggtgtgggtg atttcctggc gggggagca     120 gccaggtgag cccaagatgc tgctgcgctc gaagcctgcg ctgccgccgc cgctgatgct    180
gctgctcctg gggccgctgg gtcccctctc ccctggcgcc ctgccccgac ctgcgcaagc    240
acaggacgtc gtggacctgg acttcttcac ccaggagccg ctgcacctgg tgagcccctc    300
gttcctgtcc gtcaccattg acgccaacct ggccacggac ccgcggttcc tcatcctcct    360
gggttctcca aagcttcgta ccttggccag aggcttgtct cctgcgtacc tgaggtttgg    420
tggcaccaag acagacttcc taattttcga tcccaagaag gaatcaacct ttgaagagag    480
```

-continued

| | |
|---|---|
| aagttactgg caatctcaag tcaaccagga tatttgcaaa tatggatcca tccctcctga | 540 |
| tgtggaggag aagttacggt tggaatggcc ctaccaggag caattgctac tccgagaaca | 600 |
| ctaccagaaa aagttcaaga acagcaccta ctcaagaagc tctgtagatg tgctatacac | 660 |
| ttttgcaaac tgctcaggac tggacttgat ctttggccta aatgcgttat taagaacagc | 720 |
| agatttgcag tggaacagtt ctaatgctca gttgctcctg gactactgct cttccaaggg | 780 |
| gtataacatt tcttgggaac taggcaatga acctaacagt ttccttaaga aggctgatat | 840 |
| tttcatcaat gggtcgcagt taggagaaga ttttattcaa ttgcataaac ttctaagaaa | 900 |
| gtccaccttc aaaaatgcaa aactctatgg tcctgatgtt ggtcagcctc gaagaaagac | 960 |
| ggctaagatg ctgaagagct tcctgaaggc tggtggagaa gtgattgatt cagttacatg | 1020 |
| gcatcactac tatttgaatg gacggactgc taccagggaa gattttctaa accctgatgt | 1080 |
| attggacatt tttatttcat ctgtgcaaaa agttttccag gtggttgaga gcaccaggcc | 1140 |
| tggcaagaag gtctggttag gagaaacaag ctctgcatat ggaggcggag cgcccttgct | 1200 |
| atccgacacc tttgcagctg gctttatgtg gctggataaa ttgggcctgt cagcccgaat | 1260 |
| gggaatagaa gtggtgatga ggcaagtatt cttggagca ggaaactacc atttagtgga | 1320 |
| tgaaaacttc gatcctttac ctgattattg gctatctctt ctgttcaaga aattggtggg | 1380 |
| caccaaggtg ttaatggcaa gcgtgcaagg ttcaaagaga aggaagcttc gagtatacct | 1440 |
| tcattgcaca aacactgaca atccaaggta taagaagga gatttaactc tgtatgccat | 1500 |
| aaacctccat aatgtcacca agtacttgcg gttaccctat ccttttttcta acaagcaagt | 1560 |
| ggataaatac cttctaagac ctttgggacc tcatggatta cttttccaaat ctgtccaact | 1620 |
| caatggtcta actctaaaga tggtggatga tcaaaccttg ccacctttaa tggaaaaaacc | 1680 |
| tctccggcca ggaagttcac tgggcttgcc agctttctca tatagttttt ttgtgataag | 1740 |
| aaatgccaaa gttgctgctt gcatctgaaa ataaaatata ctagtcctga cactgaattt | 1800 |
| ttcaagtata ctaagagtaa agcaactcaa gttataggaa aggaagcaga taccttgcaa | 1860 |
| agcaactagt gggtgcttga gagacactgg gacactgtca gtgctagatt tagcacagta | 1920 |
| ttttgatctc gctaggtaga acactgctaa taataatagc taataatacc ttgttccaaa | 1980 |
| tactgcttag cattttgcat gttttacttt tatctaaagt tttgtttttgt tttattattt | 2040 |
| atttatttat ttattttgtg acggagagag attccatctc aaaaaaacaa gttattaaaa | 2100 |
| atgtatatga atgctcctaa tatggtcagg aagcaaggaa gcgaaggata tattatgagt | 2160 |
| tttaagaagg tgcttagctg tatatttatc tttcaaaatg tattagaaga ttttagaatt | 2220 |
| cttttccttca tgtgccatct ctacaggcac ccatcagaaa aagcatactg ccgttaccgt | 2280 |
| gaaactggtt gtaaaagaga aactatctat ttgcacctta aaagacagct agattttgct | 2340 |
| gattttcttc tttcggtttt ctttgtcagc aataatatgt gagaggacag attgttagat | 2400 |
| atgatagtat aaaaaatggt taatgacaat tcagaggcga ggagattctg taaacttaaa | 2460 |
| attactataa atgaaattga tttgtcaaga ggataaattt tagaaaacac ccaataccttt | 2520 |
| ataactgtct gttaatgctt gcttttttctc tacctttctt ccttgtttca gttgggaagc | 2580 |
| ttttggctgc aagtaacaga aactcctaat tcaaatggct taagcaataa ggaaatgtat | 2640 |
| attcccacat aactagacgt tcaaacaggc caggctccag cacttcagta cgtcaccagg | 2700 |
| ggatctgggt tcttcccagc tctctgctct gccatcttta cgctggctt cattctcaga | 2760 |
| ctctggtagc atgatggctg tagctgtttc atgggcccct tcaaacctca tagcaaccag | 2820 |
| aggaagaaaa tgagccattt tttgagtctc cttcatagac ttgaataact cttttttcaga | 2880 |

-continued

```
gcttctcaca gcaaacctct cctcatgtct cctcatgtct tattgttcag aaatgggtaa      2940
tgtggccatt tcaccagtca ctgccaacaa caacgaggtt cctataattg tctctgagta      3000 acectttgga atggagaggg tgttggtcag tctacaaact gaacactgca gttctgcgct      3060
ttttaccagt gaaaaaatgt aattattttc ccctcttaag gattaatatt cttcaaatgt      3120
atgcctgtta tggatatagt atctttaaaa ttttttattt taatagcttt agggtacac       3180 acttttgct tacagggtg aattgtgtag tggtgaagac tcggctttta atgtacttgt        3240
cacctgagtg atgtacattg tacccaatag gtaattttc atccattacc ctccttccgc      3300
cctcttccct tctgagtctc caacatccct tataccactg tgtatgttct tgtgtaccta      3360
cagctaagct tccacttata agtgagaaca tgcagtattt ggttttccat tcctgagtta      3420
cttcccttag gataacagcc cccagttccg tccaagttgc tgcaaaatac attattcttc     3480
tttatggctg agtaatagtc catggtacat atataccaca ttttctttat ccacttatca      3540
gttgatggac acttaggtta attccattca atttcattca atttaagtat atttgtaagg     3600
agctaaagct gaaaattaaa ttttagatct ttcaatactc ttaaatttta tatgtaagtg     3660 gttttttatat tttcacattt gaaataaagt aattttata accttgaaaa aaaaaaaaa      3720 aaaaaa                                                                3726
```

<210> SEQ ID NO 2
<211> LENGTH: 588
<212> TYPE: PRT
<213> ORGANISM: Human

<400> SEQUENCE: 2

```
Ser Ala Ala Pro Arg Ala Leu Leu Pro Gly Arg Ser Pro Gly Leu
  1               5                  10                  15

Pro Gly Ala Trp Ile Pro Ala Ile Ser Ala Pro Phe Lys Trp Val Trp
             20                  25                  30

Val Ile Ser Trp Arg Gly Glu Gln Pro Gly Glu Pro Lys Met Leu Leu
         35                  40                  45

Arg Ser Lys Pro Ala Leu Pro Pro Leu Met Leu Leu Leu Leu Gly
     50                  55                  60

Pro Leu Gly Pro Leu Ser Pro Gly Ala Leu Pro Arg Pro Ala Gln Ala
 65                  70                  75                  80

Gln Asp Val Val Asp Leu Asp Phe Phe Thr Gln Glu Pro Leu His Leu
                 85                  90                  95

Val Ser Pro Ser Phe Leu Ser Val Thr Ile Asp Ala Asn Leu Ala Thr
             100                 105                 110

Asp Pro Arg Phe Leu Ile Leu Leu Gly Ser Pro Lys Leu Arg Thr Leu
         115                 120                 125

Ala Arg Gly Leu Ser Pro Ala Tyr Leu Arg Phe Gly Gly Thr Lys Thr
     130                 135                 140

Asp Phe Leu Ile Phe Asp Pro Lys Lys Glu Ser Thr Phe Glu Glu Arg
145                 150                 155                 160

Ser Tyr Trp Gln Ser Gln Val Asn Gln Asp Ile Cys Lys Tyr Gly Ser
                 165                 170                 175

Ile Pro Pro Asp Val Glu Lys Leu Arg Leu Glu Trp Pro Tyr Gln
             180                 185                 190

Glu Gln Leu Leu Leu Arg Glu His Tyr Gln Lys Phe Lys Asn Ser
         195                 200                 205

Thr Tyr Ser Arg Ser Ser Val Asp Val Leu Tyr Thr Phe Ala Asn Cys
```

```
                  210                 215                 220
Ser Gly Leu Asp Leu Ile Phe Gly Leu Asn Ala Leu Leu Arg Thr Ala
225                 230                 235                 240

Asp Leu Gln Trp Asn Ser Ser Asn Ala Gln Leu Leu Leu Asp Tyr Cys
                245                 250                 255

Ser Ser Lys Gly Tyr Asn Ile Ser Trp Glu Leu Gly Asn Glu Pro Asn
                260                 265                 270

Ser Phe Leu Lys Lys Ala Asp Ile Phe Ile Asn Gly Ser Gln Leu Gly
                275                 280                 285

Glu Asp Phe Ile Gln Leu His Lys Leu Leu Arg Lys Ser Thr Phe Lys
290                 295                 300

Asn Ala Lys Leu Tyr Gly Pro Asp Val Gly Gln Pro Arg Arg Lys Thr
305                 310                 315                 320

Ala Lys Met Leu Lys Ser Phe Leu Lys Ala Gly Gly Glu Val Ile Asp
                325                 330                 335

Ser Val Thr Trp His His Tyr Tyr Leu Asn Gly Arg Thr Ala Thr Arg
                340                 345                 350

Glu Asp Phe Leu Asn Pro Asp Val Leu Asp Ile Phe Ile Ser Ser Val
                355                 360                 365

Gln Lys Val Phe Gln Val Val Glu Ser Thr Arg Pro Gly Lys Lys Val
370                 375                 380

Trp Leu Gly Glu Thr Ser Ser Ala Tyr Gly Gly Gly Ala Pro Leu Leu
385                 390                 395                 400

Ser Asp Thr Phe Ala Ala Gly Phe Met Trp Leu Asp Lys Leu Gly Leu
                405                 410                 415

Ser Ala Arg Met Gly Ile Glu Val Val Met Arg Gln Val Phe Phe Gly
                420                 425                 430

Ala Gly Asn Tyr His Leu Val Asp Glu Asn Phe Asp Pro Leu Pro Asp
                435                 440                 445

Tyr Trp Leu Ser Leu Leu Phe Lys Lys Leu Val Gly Thr Lys Val Leu
                450                 455                 460

Met Ala Ser Val Gln Gly Ser Lys Arg Arg Lys Leu Arg Val Tyr Leu
465                 470                 475                 480

His Cys Thr Asn Thr Asp Asn Pro Arg Tyr Lys Glu Gly Asp Leu Thr
                485                 490                 495

Leu Tyr Ala Ile Asn Leu His Asn Val Thr Lys Tyr Leu Arg Leu Pro
                500                 505                 510

Tyr Pro Phe Ser Asn Lys Gln Val Asp Lys Tyr Leu Leu Arg Pro Leu
                515                 520                 525

Gly Pro His Gly Leu Leu Ser Lys Ser Val Gln Leu Asn Gly Leu Thr
                530                 535                 540

Leu Lys Met Val Asp Asp Gln Thr Leu Pro Pro Leu Met Glu Lys Pro
545                 550                 555                 560

Leu Arg Pro Gly Ser Ser Leu Gly Leu Pro Ala Phe Ser Tyr Ser Phe
                565                 570                 575

Phe Val Ile Arg Asn Ala Lys Val Ala Ala Cys Ile
                580                 585
```

HUMAN HEPARANASE POLYPEPTIDE AND CDNA

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, a polypeptide of the present invention is "heparanase" obtainable from the human SV40-transformed fibroblast cell line ATCC CCL 75.1. The heparanase is an endoglucuronidase capable of specifically degrading heparan sulfate into 6 to 20 kDa fragments. The invention also relates to vectors and host cells, comprising a polynucleotide of the invention. Furthermore, the present invention relates to antibodies directed to polypeptides according to the present invention, to pharmaceutical compositions comprising such antibodies or polypeptides, and to assay systems suitable for identifiying agonists or antagonists of such polypeptides.

BACKGROUND OF THE INVENTION

Heparanase was first identified in murine metastatic melanoma cells by Nakajima et al. (Nakajima et al., Science 220: 611–613, 1983). They concluded the heparan sulfate degrading enzyme responsible is an endoglucuronidase, cleaving linkage between GIcA and GIcNAc, and named it heparanase (Nakajima et al., J. Biol. Chem. 259: 2283–2290, 1984). The heparanase is a hydrolase distinguished from Flavobacterium heparitinase and heparinase (Ototani, N. et al., Carbohydrate Res. 88: 291–303, 1981) which are eliminases capable of specifically degrading heparan sulfate and heparin, respectively into di- and tetra-saccharides (Nakajima et al., J. Biol. Chem. 259: 2283–2290, 1984).

Heparanase-like activity has been found in several normal and tumor cells and tissues as reviewed by Nakajima et al. (J. Cell. Biochem. 36: 157–167, 1988). According to the reports from various laboratories the existance of at least three different types of heparin and/or heparan sulfate-degrading endoglucuronidase has been predicted. The melanoma heparanase degrades heparan sulfate but is not active on heparin. The human platelet heparanase depolymerizes both heparin and heparan sulfate and cleaves β-glucuronidic linkages in the antithrombin-binding domain of heparin (Thunberg et al., J. Biol. Chem. 257:10278–10282, 1982). Another endoglucuronidase from mastocytoma cells catalyzes the depolymerization of macromolecular heparin proteoglycans into fragments similar in size to commercial heparin (Ögren and Lindahl, J. Biol. Chem. 250:2690–2697, 1975). The mastocytoma enzyme has little or no activity against heparan sulfate and does not cleave the antithrombin-binding regions of heparin.

The enzymatic characteristics of heparanase have been studied in several laboratories. Nakajima et al. found that heparanase does not degrade highly sulfated heparin of porcine mucosa and bovine lung, chondroitin 4-sulfate, chondroitin 6-sulfate, dermatan sulfate, and hyaluronic acid (Nakajima et al., J. Biol. Chem. 259: 2283–2290,1984). They also reported that heparanase is inhibited by heparin described above but not by an exoglucuronidase inhibitor, 1,4-saccharolactone (Nakajima et al., J. Biol. Chem. 259: 2283–2290,1984). Highly sulfated heparan sulfate produced by vascular endothelial cells is relatively resistant to heparanase as compared with bovine lung and kidney heparan sulfate and is cleaved by heparanase into large molecular size fragments (Nakajima et al., J. Biol. Chem. 259: 2283–2290, 1984). Thus they suggested the domain structures of heparan sulfate recognized by heparanase. Bai, X. et al (J. Biol. Chem. 272: 23172–23179, 1997) have recently shown with a use of a mutant cell line of CHO cell that 2-O-sulfate uronic acid is important for heparanase recognition of heparan sulfate and its enzymatic activity. Bame, K. J. et al (J. Biol. Chem. 272: 2245–2251, 1997) have predicted the existance of two types of heparanase, one cleaving near the reducing end and the other cleaving near the non-reducing end of highly sulfated region of heparan sulfate. Schmidtchen, A. et al. (Eur. J. Biochem. 223: 211–221, 1994) have also proposed the model of heparanase cleavage site from experiments that heparanase treatment generated low-sulfated, GIcNAc-containg heparan sulfate fragments of approximately 7 kDa in molecular size.

Various methods for detecting heparanase activity are reported including (i) polyacrylamide gel electrophoresis (Nakajima, M. et al., Science 220: 611–613, 1983), (ii) gel filtration chromatography (Nakajima, M. et al., J. Biol. Chem. 259: 2283–2290, 1984), (iii) high speed gel permeation chromatography (Irimura, T. et al., Anal. Biochem, 130: 461–468, 1983) (iv) solid-phase substrates of heparanase (Nakajima, M. et al., Anal. Biochem. 157: 162–171, 1986; U.S. Pat. No. 4,859,581), (v) radio-labeled and florescein-labeled heparan sulfate for detection of heparanase activity (U.S. Pat. No. 4,859,581, WO 9504158A), (vi) use of chicken histidine rich glycoprotein (cHRG), taking advantage that heparanase treated heparan sulfate fragment has low affinity to cHRG.

Various methods for purifying heparanase have been disclosed in WO 9102977A and WO 9504158A: the former is a method for preparation of the native heparanase by using chromatographic procedure, and the later is a method for purifying heparanase having activity of endo-N-acetylglucosaminidase.

Biochemical, biological, and pathological studies of heparan sulfate proteoglycans have led to examine the role of heparanase in various diseases. Heparan sulfate is a major component of basement membranes which are continuous sheets of extracellular matrices separating parenchymal cells from underlying interstitial connective tissues. Basement membranes have characteristic permeability and play a role in maintaining normal tissue architecture. Heparan sulfate proteoglycans promote basal lamina matrix assembly by enhancing the interactions of collagenous and noncollagenous protein components while protecting them against proteolytic attack. Heparan sulfate is also a real barrier against cationic and large molecules in the basement membrane. Thus, the destruction of heparan sulfate proteoglycan barrier is an important step during the penetration of basement membranes by both normal and tumor cells (Nakajima, M. et al., J. Cell. Biochem. 36:157–167, 1988).

Most cancer mortality is the result of metastasis to regional and distant metastases. Metastasis formation occurs via a sequential and complex series of unique interactions between tumor cells and normal host cells and tissues. During the metastasis formation migrating tumor cells confront natural barriers such as connective tissues and basement membranes. The ability of malignant cells to penetrate these barriers depends on the presence of tumor and/or host enzymes capable of degrading stromal and basement membrane components. In fact several tumor cell-associated proteinases and glycosidases have been implicated in the tumor cell invasion and metastasis and their activities correlate with metastatic potential in several types of malignant cells. The enzymatic degradation of heparan sulfate proteoglycans in vascular subendothelial basement membranes followed by release of heparan sulfate fragments are achieved by metastatic tumor cells, angiogenic endothelial cells, and inflammatory cells. A good correlation between heparanase activity and metastatic potential has been found in several types of malignant tumors such as melanoma, T cell lymphoma, fibrosarcoma, and rhabdomyosarcoma (Nakajima et al., Science220: 611, 1983; Vlodavsky et al., Cancer Res. 43: 2704, 1983; Ricoveri and Cappelletti, Cancer Res. 46: 3855, 1986; Becker et al., J. Natl. Cancer Inst. 77: 417, 1986).

Similar observations have been reported from several other laboratories using different types of tumors as reviewed by Nakajima et al. (J. Cell. Biochem. 36: 157–167, 1988) and Vlodavsky et al. (Cancer Metastasis Rev., 9: 203–226, 1990), suggesting that heparanase plays a critical role in cell penetration through vascular basement membranes during the blood-borne metastasis, angiogenesis, and inflammatory cell migration. Therefore, heparanase inhibition leads to suppression of tumor cell extravasation and angiogenesis resulting in the inhibition of tumor metastasis. U.S. Pat. No. 5,262,403A describes glycosaminoglycan derivatives and their use as inhibitors of tumor invasiveness of metastatic profusion. U.S. Pat. No. 4,882,318 describes heparin derivatives as inhibitors of tumor metastasis and angiogenesis.

Various molecules such as fibroblast growth factor (FGF), antithorombin III, platelet factor IV, vascular endothelial growth factor (VEGF), interferon-gamma (IFN-g), hepatocyto growth factor (HGF), kinases, phosphatases lipoprotein lipase, IP-10, herpes simplex virus type I are known to bind to heparan sulfate. Among all, extensive studies on interaction of bFGF and heparan sulfate have been reported from various laboratories(for review: Schlessinger, J. et al. Cell. 83: 357–360, 1995). Modulations of the interactions and bioavailability of these molecules by heparanase have been reported by several groups. Whitelock. J. M. et al. (J. Biol. Chem. 271: 10079–10086, 1996) have shown heparanase as the most efficient agent among the enzymes they have tested (plasmin, collagenase, thrombin, and stromelysin) to release bound growth factors from perlecan, one of the heparan sulfate proteoglycans. They have speculated the release of bFGF from heparan sulfate oligosaccaride chains would lead to regeneration of tissues at sites of injury in the wound healing process.

Hoogewerf. A. J. et al. have identified heparanase from human platelets and examined its enzymatic characteristics (J. Biol.Chem. 270: 3268–3277, 1995). The N-terminal amino acid sequence of heparanase from human platelets, which they identified, revealed it as Connective Tissue Activating Peptide-III (CTAP-III), one of a CXC Chemokine family, and its mode of action was an endo-N-acetylglucosaminidase, degrading heparan sulfate into dissachrides. In their discussion they referred to the dual function of CTAP-III as both a heparanase and a neutrophil chemoattractant, suggesting its functions in various pathologies. For example, heparanase activity of the chemokine could down-regulate inflammation by degrading focal sites of chemokine anchoring on the surface of the inflammed endothelium. In vascular pathologies, degradation of vascular heparan sulfate by CTAP-III would remove antithrombin III binding sites and promote thrombogenesis.

Lider et al. have shown a disaccharide that inhibits tumor necrosis factor alpha is formed from the extracellular matrix by the enzyme heparanase (Proc. Natl. Acad. Sci. U.S.A. 92: 5037–5041, 1995). When T-cells are activated by the antigens presented on antigen-presenting cells, they produce effector molecules, such as an inflammatory cytokines, tumor necrosis factor-alpha (TNF-a) and an enzyme, heparanase. As a consequence, heparanase disrupts heparan sulfate molecules in extracellular matricies and/or cell surfaces and produces dissaccharides of heparan sulfate, which in turn down-regulates the inflammatory activity of activated T-cells. The negative feedback control of T-cell mediated inflammation by heparanase implies that administering such enzyme molecules therapeutically might succeed in immune system modulation.

Gilat, D. et al. have shown that the heparanase serves as a T-cell adhesion molecule at physiological pH (J. Exp. Med. 181: 1929–1934, 1995). At a physiological pH, the relatively quiescent enzyme, heparanase appears to act as a lectin-like proadhesive molecule that can organize the recruitment of resting T cells in extravascular loci. Therefore, the heparanase-mediated ECM-anchored CD4+ T cells could readily respond to costimulatory signals elicited by specifically activated adjacent immune cells.

Beta-amyloid is a major component of the senile plaques characteristic of Alzheimer's disease (Snow, A. D. et al., Neuron 12: 219–234, 1996). Histochemical and immunocytochemical studies have shown that heparan sulfate proteoglycans and glycosaminoglycans colocalize with beta-amyloid protein in senile plaques of Alzheimer's disease. McCubbin et al (Biochem J. 256: 775–783, 1988) have shown that heparan sulfate removed all the random coil structure of serum amyloid polypeptide and converted into beta-sheet beta-turn conformation leading to aggregation of amyloid-beta fibrils. Glypican, one of heparan sulfate proteoglycans was shown to binds to the amyloid precursor protein of Alzheimer's disease and inhibits amyloid precursor protein-induced neurite outgrowth (Williamson et al., J. Biol. Chem. 271: 31215–31221, 1996). These findings suggest that one mechanism to prevent the complex formation of beta-amyloid with heparan sulfate proteoglycan that lead to deposition of amyloid would be to degrade the proteoglycan. Small molecules, which mimic elements of the heparan sulfate structure, can interfere with both in vivo induction and persistence of amyloid protein, and furthermore can interfere with the induction of amiloid beta-sheet formation and the amyloid-beta fibrinogenesis in vitro by heparan sulfate (Kisilevsky et al., Nature Med. 1: 143–148, 1995). Thus, heparanase capable of degrading heparan sulfate can be used as a therapeutic tool to prevent beta-amyloid deposition in senile plaques.

In view of the various features of enzymes showing heparanase-like activities, which are well suited for use in the pharmaceutical field, there is an ongoing need to provide further polypeptides showing such activities. Preferably, such polypeptides show an advantageous behaviour compared to that of known enzymes. Moreover, there is a need for providing a polynucleotide encoding such a polypeptide, in order to be able to prepare sufficient amounts of such a polypeptide by means of recombinant expression technologies.

SUMMARY OF INVENTION

The present invention relates to polypeptide showing the biological activity of human heparanase obtainable from the SV-40 transformed human fibroblast cell line ATCC CCL 75.1, or a functional derivative, a functional fragment or a functional analogue thereof.

The present invention further relates to a polynucleotide comprising a nucleotide sequence encoding a such a polypeptide.

In another aspect the invention relates to a process for preparing such a polypeptide or such a polynucleotide.

Moreover, the present invention relates to a hybrid vector comprising such a polynucleotide, and to a host cell transformed with such a hybrid vector.

It is a further object of the present invention to provide an antibody specifically recognizing and binding to such a polypeptide and to a method of diagnosis utilizing such an antibody.

Further objects of the present invention relate to pharmaceutical compositions comprising such a polypeptide or antibody, and to a method of treatment comprising administration of such a polypeptide or antibody.

In a yet further aspect the present invention provides an assay system and a method for identifying a substance capable of modulating the biological activity or expression of such a polypeptide, and substances obtainable by such a method.

Another aspect of the present application relates to an oligonucleotide or a derivative thereof capable of specifically hybridizing with a polynucleotide according to the present invention.

In a further aspect, the present invention is directed to the use of such a polynucleotide in gene therapy.

DETAILED DESCRIPTION OF THE INVENTION

In accordance with one aspect of the present invention, there is provided a polypeptide showing the biological activity of human heparanase obtainable from SV-40 transformed human fibroblast cell line ATCC CCL 75.1, or a functional derivative, a functional fragment or a functional analogue thereof. In particular, such a polypeptide is an endoglucuronidase capable of specifically cleaving heparan sulfate into fragments having a size range of from about 6 kDa to about 20 kDa. Said human cell line is the cell line WI-38 VA 13 subline 2RA, available from ATCC (American Type Culture Collection) under accession number ATCC CCL 75.1. It is an SV40 virus-transformed derivative of the WI-38 fibroblast cell line (ATCC CCL 75), which is a diploid cell line from normal embryonic (3-month gestation) lung tissue of a Caucasian female.

In a preferred embodiment thereof a polypeptide according to the present invention is the mature form of the polypeptide having the amino acid sequence set forth in SEQ ID NO 2.In particular, the mature polypeptide has the amino acid sequence of amino acids 158 to 543 set forth in SEQ ID NO 2.

The polypeptide having the amino acid sequence set forth in SEQ ID NO 2 (i.e. amino acids 1 to 543) is the predicted precursor form of the protein where approximately the first 24 amino acids represent the leader sequence and the first 157 amino acids are the prosequence. Such a precursor polypeptide forms another aspect of the present invention.

The present invention further provides a process for the preparation of a polypeptide of the invention, said process comprising chemical synthesis, recombinant DNA technology or a combination of these methods.

In accordance with another aspect of the present invention, there is provided an isolated nucleic acid molecule (polynucleotide) comprising a nucleotide sequence encoding a polypeptide according to the present invention, i.e. a polypeptide showing the biological activity of human heparanase obtainable from SV-40 transformed human fibroblast cell line ATCC CCL 75.1, or coding for the amino acid sequence of a functional derivative, a functional fragment or a functional analogue thereof. Preferably such a polynucleotide comprises a nucleotide sequence encoding such a polypeptide having the amino acid sequence of amino acids 158 to 543 set forth in SEQ ID NO 2, said polypeptide being the mature form of the heparanase of the present invention. In another embodiment such polynucleotide comprises a nucleotide sequence encoding a polypeptide having the amino acid sequence of amino acids 1 to 543 set forth in SEQ ID NO 2, said polypeptide being the precursor form of the heparanase of the present invention. Another preferred embodiment of the present invention relates to a polynucleotide having the nucleotide sequence set forth in SEQ ID NO 1.

A polynucleotide encoding a polypeptide of the present invention may be obtained from a cDNA library derived from human carcinoma cells, placenta, peripheral blood leucocytes, or lung. In particular, the polynucleotide described herein is isolated from a cDNA library derived from human SV-40 transformed fibroblast cell line ATCC CCL 75.1. The cDNA insert is 3726 base pairs (bp) in length and contains an open reading frame encoding a protein 543 amino acids in length of which approximately the first 24 amino acids represent the leader sequence and first 157 amino acids represent the prosequence. Thus, the mature form of the polypeptide of the present invention consists of 386 amino acids after the 157 amino acid prosequence (which includes the approximately 24 amino acid leader sequence) is cleaved. The polypeptide may be found in lysosomes of, or extracellularly near, carcinoma cells.

The polynucleotide of the present invention may be in the form of RNA or in the form of DNA, which RNA includes mRNA and pre-mRNA, and which DNA includes cDNA, genomic DNA and synthetic DNA. The DNA may be double-stranded or single-stranded, and if single stranded may be the coding strand or non-coding (anti-sense) strand. The coding sequence which encodes the mature polypeptide or the precursor form may be identical to the coding sequence contained in SEQ ID NO 1, or may be different from that coding sequence, as a result of the redundancy or degeneracy of the genetic code, but encodes the same, mature polypeptide or the precursor form thereof as the cDNA of SEQ ID NO 1.

In preferred embodiments, the polynucleotide according to the present invention may include: only the coding sequence for mature polypeptide; the coding sequence for the leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide comprising a nucleotide sequence encoding a polypeptide" encompasses a polynucleotide which includes only coding sequence for the polypeptide as well as a polynucleotide which includes one or more additional coding and/or non-coding sequences.

The present invention further relates to variants of the hereinabove described polynucleotides which encode for fragments, analogs and derivatives of the polypeptide having the deduced amino acid sequence of SEQ ID NO 2. The variant of the polynucleotide may be a naturally occurring allelic variant of the polynucleotide or a non-naturally occurring variant of the polynucleotide. The present invention also relates to polynucleotide probes constructed form the polynucleotide sequence of SEQ ID NO 1 or a segment of the sequence of SEQ ID No 1 amplified by the PCR method, which could be utilized to screen an above mentioned cDNA library to deduce the polypeptide of the present invention.

Thus, the present invention includes polynucleotides encoding the same mature polypeptide of the present invention as well as variants of such polynucleotides which variants encode for a fragment, derivative or analog of such a polypeptide. Such nucleotide variants include deletion variants, substitution variants and addition or insertion variants.

As hereinabove indicated, the polynucleotide may have a coding sequence which is a naturally occurring allelic variant of the coding sequence of SEQ ID NO 1. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a controlling transport of a polypeptide from the cell. The polypeptide having a leader sequence is a preprotein and may have the leader sequence cleaved by the host cell to form a mature form of the polypeptide. The polynucleotides may also encode for a pro-protein which is the mature protein plus additonal N-terminal and C-terminal amino acid residues. A mature protein having a prosequence is a pro-protein and may in some cases be an inactive form of the protein. Once the prosequence is cleaved an active mature protein remains.

Thus, for example, the polynucleotide of the present invention may encode for a mature protein, or for a protein having a prosequence or for a protein having both a presequence (leader sequence) and a prosequence.

The polynucleotides of the present invention may also have the coding sequence fused in frame to a marker-sequence which allows for purification of the polypeptide of the present invention. The marker sequence may be a hexa-histidine tag supplied by a pProEX-HTb (Gibco BRL) vector to provide for purification of the mature polypeptide fused to the marker in the case of a bacterial host, or, for example, the marker sequence may be a hemagglutinin (HA) tag when a mammalian host, e.g. COS7 cells, is used. The HA tag corresponds to an epitope derived from the influenza hemagglutinin protein (Wilson, I., et al. Cell, 37:767 (1984)).

A polynucleotide according to the present invention can be prepared by a process comprising chemical synthesis, recombinant DNA technology, polymerase chain reaction or a combination of these methods. Such a process forms a further aspect of the present invention.

The terms "functional fragment," "junctional derivative" and "functional analogue" when referring to a polypeptide according to the present invention, means a polypeptide which retains essentially the same biological function or activity as such polypeptide. Thus, an analogue may include a proprotein portion to produce an active mature polypeptide.

The polypeptide of the present invention may be a recombinant polypeptide, a natural polypeptide or a synthetic polypeptide, preferably a recombinant polypeptide.

The functional fragment, derivative or analog of a polypeptide of the present invention may be (i) one in which one or more of the amino acid resideus are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity. The term "isolated" means that the material is removed from its original environment (e.g., the natural environment if it is naturally occuring). For example, a naturally-occuring polynucleotide or polypeptide present in a living animal is not isolated, but the same polynucleotide (e.g. a DNA or a RNA molecule) or polypeptide, separated from some or all of the coexisting materials in the natural system, is isolated. A polynucleotide of the present invention could be a part of a vector and/or such a polynucleotide or polypeptide could be a part of a composition, and still be isolated in that such a vector or composition is not a part of its natural environment.

The present invention also relates to a hybrid vector comprising a polynucleotides of the present invention, said hybrid vector being operably linked to suitable control sequences. Preferably, such a hybrid vector is an expression vector. Furthermore, the present invention relates to a host cell transformed with a hybrid vector of the present invention, i.e. which host cell is genetically engineered with such a hybrid vector. In another aspect, the present invention relates to a recombinant process for the preparation of a polypeptide of the present invention, said process comprising (i) cultivation of a host cell transformed with a hybrid vector of the present invention under conditions suitable for performing expression of the polypeptide, and (ii) isolation of the thus-expressed polypeptide.

Host cells are genetically engineered (transduced or transformed or transfected) with the vectors of this invention which may be, for example, a cloning vectors or an expression vector. The vector may be, for example, in the form of a plasmid, a viral particle, a phage, etc.

The engineered host cells can be cultured in conventional nutrient media modified as appropriate for activating promotes, selecting transformants or amplifying the Heparanase gene. The culture conditions, such as temperature, pH and the like, are those used with the host cell selected for expression, and will be apparent to the ordinarily skilled art.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmid; vectors derived from combinations of plasmids and phage DNA, viral DNA such as vaccinia, adenovirus, fowl pox virus, baculovirus, and pseudorabies. However, any other plasmid or vector may be used as long as it is replicable and viable in the host.

As hereinabove indicated, the appropriate DNA sequence may be inserted into the vector by a variety of procedures. In general, the DNA sequence is inserted into appropriate restriction endonuclease sites by procedures known in the art.

The DNA sequence in the expression vector is operatively linked to (an) appropriate expression control sequence(s) (promoter) to direct mRNA synthesis. As representative examples of such promoters, there may be mentioned: LTR or SV40 promoter, the E.coli. lac or trp, the expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E.coli.

The vector containing the appropriate DNA sequence as hereinabove described, as well as an appropriate promoter or control sequence, may be employed to transform an appropriate host to permit the host to express the protein. As representative examples of an appropriate host, there may be mentioned: bacterial cells, such as E.coli, Salmonella typhimurium; Streptomyces; fungal cells, such a s yeast; insect cells such as Drosophila and Sf9; animal cells such as CHO and COS; plant cells, etc. The selection of an appropriate host is deemed to be within the scope of those skilled in the art fom the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverese orientation. The construct further comprises regulatory sequences, including, for example, a promoter, operably linked to the sequence. Large numbers of suitable vectors and promoters are known to those of skill in the art, and are commercially available. The following vectors are provided by way of example. Bacterial:pQE70, pQE60, pQE-9 (Qiagen)pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particularly named bacterial promoters include lac, lacZ, T3, T7, gpt, lambda PR, PI and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. In a further embodiment, the present invention relates to host cells containing the above-described construct. The host cell can be a higher eukaryotic cell such as mammalian cell, or a lower eukaryotic cell, such as a yeast cell, e.g. S. cerevisiae, or the host cell can be a prokaryotic cell, such as a bacterial cell, e.g. E. coli. Introduction of the construct into the host cell can be effected by clacium phospahe transfection, DEAE-Dextran mediated trasfection, or electorporation (Davis, L., Dibner, M., Battey I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA costructs of the present invention. Appropriate cloning an expression vectors for use with prokaryotic and eukaryotic hosts are described by Sambrook. Et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 19 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S cerevisiae TRP1 gene, and a promoter derived form a highly-expressed gene to direct transcription of a downstream structural sequence. Such promoters can be derived from operons encoding glycolytic enzymes such as 3-phosphoglycerate kinase (PGK), alpha factor, acid phosphatase or heat shock proteins, among others. The heterologous structural sequence is assembled in appropriate phase with translation initiation and termination sequences, and preferably, a leader sequence capable of directing secretion of a translated protein into the periplasmic space or extracellular medium. Optionally, the heterologous sequence can encode a fusion protein including an N-terminal identification peptide imparing desired characteristics, e.g., stabilization or simplified purificatio of expressed recominant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vetor and to, if desirable, provide amplification within the host. Suitable prokaryotic hosts for transformation include E.coli, Bacillus subilis, Salmonellatyphimurium and various species within the genera Pseudomonas, Streptomyce, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBK322 (ATCC37017). Such commercial vectors include, for, example, PKK223–3 (Pharmacia) and GEM1 (Promega Biotec, Madison, Wis., USA). These pBR3222 "backbone" sections are combined with an appropriate promoter and structural sequence to be expressed. Various mammalian cell culture systems can also be employed to express recombint protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flaking nontranscribed sequences. DNA sequences derived from the SV40 viral genome for example, SV40 origin, early promoter, enhancer, splice, and polyadenylation sites may be used to provide the required nontranscribed genetic elements.

A thus-expressed polypeptide of the present invention is recovered and purified from recombinant cell cultures by methods used heretofore, including detergent homoginates, Heparin-Sepharose chromatography, cation exchange chromatography, Con A-Sepharose chromatography, gel-filtration chromatography, and hydrophobic interaction chromatography.

A polypeptide of the present invention may be purified products naturally expressed from a high expressing cell line, or a product of chemical synthetic procedures, or produced by recombinant techniques from a prokaryotic or eukaryotic host (hor example, by bacterial, yeast, higher plant, insect and mammalian cells in culture). Depending upon the host employed in a recombinant production procedure, a polypeptide of the present invention may be glycosylated with mammalian or other eukaryotic carbohydrates or may be non-glycosylated. A polypeptide of the invention may also include an initial methionine amino acid residue.

The polynucleotides of the present invention are also valuable for chromosome identification. The polynucleotide is specifically targeted to and can hybridize with a particular location on an individual human chromosome. Moreover, there is a current need for identifying paricular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with diseases.

Briefly, sequences can be mapped to chromosomes by preparing PCR primers (preferably 15–25b bp) from the cDNA Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes* a Manual of Basic Techniques. Pergamon Press, New York (1988).

Once a sequence has been mapped to a precise chromosomal location, the physical positio of the sequence on the chromosome can be correlated with genetic map data. (Such data are found, for example, in V. McKusck, Mendelian Inheritance in Man (available on line through Johns Hopkins University welch Medical Library). The relationship between genes and diseases that have been mapped to the same chromosomal region are then identified through linkage analysis (coinheritance of physicall adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb)

Comparison of affected and unaffected individuals generally involves first looking for structural alterations in the chromosomes, such as deletions or translocations that are visible form chromosome spreads or detectable using PCR based on that cDNA sequence. Ultimately, complete sequencing of gened from several individuals is required to confirm the presence of a mutation and to distinguish mutations from polymorphisms.

In another aspect the present invention relates to an oligonucleotide or a derivative thereof, or a salt thereof where salt-forming groups are present, which is specifically hybridizable with the nucleotide sequence set forth in SEQ ID NO 1, said oligonucleotide or derivative thereof comprising nucleoside units or analogues of nucleoside units sufficient in number and identity to allow such hybridization.

Such an oligonucleotide may have a length of, e.g., from about 5 to about 100 or to even several hundred nucleoside units or analogs thereof, depending on the intended use.

An oligonucleotide of the invention may be used as a cloning or sequencing primer or probe. Another use relates to stimulating and inhibiting a polypeptide of the present invention in vivo by the use of sense or anti-sense technology. These technology can be used to control gene expression through triple-helix formation on double-stranded DNA or antisense-mechanisms on RNA, both of which methods are based on binding of such an oligonucleotide to DNA or RNA. For example, the 5' coding portion of the polynucleotide sequence, which encodes for the mature polypeptide of the present invention, is used to design an antisense RNA oligonucleotide of from about 10 to about 40 base pairs in length. A DNA oligonucleotide is designed to be complementary to a region of the gene involved in transcription (for triple-helix technology see Lee et al, Nucl. Acids Res., 6:3073 (1979); Cooney et al, Science, 241:456 (1988); and Dervan et al, Science, 251:1360 (1991)), thereby preventing transcription and the production of Heparanase. The antisense RNA oligonucleotide hybridizes to the mRNA in vivo and blocks translation of an mRNA molecule into a polypeptide of the present invention (for antisense—technology see Okano, J. Neuroch., 56:569 (1991); Oligodeoxynucleotides as Antisense inhibitors of Gene Expression, CRC Press, Boca Raton, Fla. (1988)).

Alternatively, the oligonucleotides described above can be delivered to cells by procedures in the art such that the anti-sense RNA or DNA may be expressed in vivo to inhibit production of a polypeptide of the present invention in the manner described above.

Antisense constructs to a polypeptide of the invention, therefore inhibit the action of such a polypeptide and may be used for treating certain disorders, for example, cancer and cancer metastasis, since elevated levels of such a polypeptide is found in highly metastatic cell lines.

The polypeptides, their functional fragments, derivatives or analogs thereof, or a cell expressing them can be used as an immunogen to produce antibodies thereto.

Therfore, the present invention relates to an antibody which specifically recognizes and binds to a polypeptide of the invention.

Such an antibody can be, for example, a polyclonal or a monoclonal antibody. The present invention also includes chimeric, single chain and humanized antibodies, as well as Fab fragments, or the product of and Fab expressing library. Various procedures known in the art may be used for the production of such antibodies and fragments.

Antibodies generated against a polypeptide of the present invention can be obtained by direct injection of the polypeptide into an animal or by administering the polypeptide to an animal, preferably human. The antibody so obtained will then bind the polypeptide itself. In this manner, even a sequence encoding only a fragment of the polypeptide can be used to generate antibodies binding the whole native polypeptide. Such an antibody can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1985, Imunology Today 4:72), and the EBV-hybridoma technique to produce human monoclonal antibodies (Cole, et al., 1985, in Monoclonal Antibodies and Cancer Theraph, Alan R. Liss, Inc., pp.77–96).

Techniques described for the production of single chain antibodies (e.g. U.S. Pat. No. 4,946,778) can be adapted to produce single chain antibodies to immunogenic polypeptide products of this invention.

An antibodie specific to a polypeptide of the present invention may further be used to inhibit the biological action of the polypeptide by binding to the polypeptide. In this manner, the antibodies may be used in therapy, for example, to treat cancer since mRNA of such a polypeptide and the polypeptide itself is increased in SV-40 transformed fibroblasts.

Further, such antibodies can detect the presence or absence of a polypeptide of the present invention and the level of concentration of such polypeptide and, therefore, are useful as diagnostic markers for the diagnosis of disorders such as cancer, cancer metastasis, and angiogenesis.

Hence, the present invention relates to a method of diagnosis of conditions resulting from shortage or lack of a polypeptide of the present invention, in particular of a polypeptide showing the biological activity of human heparanase obtainable from the SV-40 transformed human fibroblast cell line ATCC CCL 75.1, or a functional derivative, a functional fragment or a functional analogue thereof, inclusive the respective preferred embodiments thereof, or resulting from excessive acitvity or overexpression of such a polypeptide, said method comprising contacting cells or tissues or body fluids from an animal inclusive man suspected of having such a condition with an antibody of the present invention.

In a further aspect, the present invention relates to a method for identifying a substance capable of modulating the biological activity or expression of a polypeptide of the present invention, said method comprising contacting such a polypeptide or a functional derivative, a functional fragment or a functional analogue thereof, or a cell capable of expressing such a polypeptide, functional derivative, functional fragment or functional analogue, with at least one compound or agent whose ability to modulate the biological activity or expression of said polypeptide is sought to be investigated, and determining the change of the biological activity or the expression of said polypeptide, derivative, fragment or analogue caused by the substance.

Another embodiment of the present invention relates to an assay system for testing a substance for its capability of binding to or having functional effects on a polypeptide of the present invention, said assay system comprising a polypeptide as of the present invention, or a functional derivative, a functional fragment or a functional analogue thereof, or a cell expressing such a polypeptide, functional derivative, functional fragment or functional analogue.

In this context, the present invention is also directed to substance obtainable by an identification-method as described above, said substance being an agonist or an antagonist of a polypeptide of the present invention.

Thus, the present invention is also directed to antagonists and inhibitors of a polypeptide of the present invention. The antagonists and inhibitors are those substances which inhibit or eliminate the function of such a polypeptide. The present invention further relates to agonists and stimulators of a polypeptide of the present invention. The agonists and stimulators are those substances which enhance the function or activity or the expression of such a polypeptide.

For example, an antagonist may bind to a polypeptide of the present invention and inhibit or eliminates its function. The antagonist, for example, could be an antibody against the polypeptide which eliminated the activity of Heparanase by binding to Heparanase, or in some cases the antagonist may be an oligonucleotide. An example of an inhibitor is a small molecule inhibitor which inactivates the polypeptide by binding to and occupying the catalytic site, thereby making the catalytic site inaccessible to a substrate, such that the biological activity of Heparanase is prevented. Examples of small molecule inhibitors include but are not limited to small carbohydrate or carbohydrate-like molecules.

In these ways, the antagonists and inhibitors may be used to treat cancer, angiogenesis by preventing heparanase from functioning to break down extracellular matrix and release heparan sulfate from extracellular matrix and cell surface.

The antagonists and inhibitors may be employed in a composition with a pharmaceutically acceptable carrier, including but not limited to saline, buffered saline, dextrose, wate, glycerol, ethanol and combinations thereof. Administration of inhibitors of the polypeptides of the present invention are preferably systemic. Suramin, a polysulfonated naphthylurea, was shown to strongly inhibit murin melanoma heparanase and its invation (Nakajima, M. et al. J. Biol. Chem. 266, p9661–9666, 1991). 2,3-O-desulfated heparin was shown to inhibit heparanase activity, tumor growth of a subcutaneous human pancreatic (Ca-Pan-2) adenocarcinoma in nude mice and prolonged the survival times of C57BL/6N mice in a B16-F10 melanoma experimental lung metastasis assay (Lapierre, F. et al. Glycobiology vol. 6, 335–366, 1996).

In particular, the present invention also relates to an assay for identifying the above-mentioned substances, e.g. small molecule inhibitors, which are specific to the polypeptides and prevent them from functioning or prevent their expression. Either natural carbohydrate substrates or synthetic carbohydrates would be used to assess endo-glycosidase activity of the polypeptide, and the ability of inhibitors to prevent this activity could be the basis for a screen to identify compounds that have therapeutic activity in disorders of excessive activity or overexpression of a polypeptide according to the present invention.

In particular, the present invention also relates to an assay for identifying the above-mentioned substances, e.g. small molecule stimulators, which are specific to the polypeptides and enhance its function or expression. Either natural carbohydrate substrates or synthetic carbohydrates would be used to assess endo-glycosidase activity of the d the ability of stimulators to enhance this activity could be the basis for a screen to identify compounds that have therapeutic activity in disorders which are resultant of shortage or lack of a polypeptide according to the present invention.

A further aspect relates to a polypeptide according to the present invention for use in medicine. In particular, the invention relates to the use of a polypeptide according to the present invention in the preparation of a pharmaceutical composition for the treatment of a disease resulting from shortage or lack of said polypeptide. Instead of a polypeptide of the present invention, an agonist of the polypeptide or an expression inducer/enhancer of such a polypeptide may be used for the medicinal purposes. Such diseases are, for example, trauma, autoimmune diseases, skin diseases, cardiovascular diseases and nervous system diseases including Alzheimer's disease.

Another aspect relates to an antibody according to the present invention for use medicine. In particular, the invention relates to the use of an antibody according to the present invention in the preparation of a pharmaceutical composition for the treatment of a disease resulting from excessive acitvity or overexpression of a polypeptide of a polypeptide according to the present invention. Instead of a antibody of the present invention, an antagonist of the polypeptide or an expression inhibitor of such a polypeptide may be used for the medicinal purposes. Such diseases are. for example, cancer, cancer metastasis, angiogenesis and inflammation including arthritis.

The invention moreover is directed to a pharmaceutical composition suitable for administration to a warm-blooded animal inclusive man suffering from a disease resulting from shortage or lack of a polypeptide of the present invention, said composition comprising such a polypeptide together with at least one pharmaceutically acceptable carrier and/or excipient. In this context, the invention is directed to a method of treatment of a disease resulting from shortage or lack of a polypeptide of the invention said method comprising administration of a suitable amount of such a polypeptide. As mentioned above, instead of such a polypeptide said composition or method of treatment may comprise or utilize an agonist of the polypeptide or an expression inducer/enhancer of such a polypeptide.

Furthermore, the invention is directed to a pharmaceutical composition suitable for administration to a warm-blooded animal inclusive man suffering from a disease resulting from excessive acitvity or overexpression of a polypeptide of the present invention, said composition comprising an antibody of the present invention together with at least one pharmaceutically acceptable carrier and/or excipient. In this context, the invention relates to a method of treatment of a disease resulting from excessive acitvity or overexpression of a polypeptide of the present invention, said method comprising administration of a suitable amount of an antibody of the present invention. As mentioned above, instead of such an antibody said composition or method of treatment may comprise or utilize an antagonist of the polypeptide or an expression inhibitor of such a polypeptide.

Further ingredients, i.e. a carrier or excipient, of a pharmaceutical composition of the present invention may be those known in the art, in particular those as decribed herein above.

In another aspect the present invention relates to a polynucleotide of the invention for use in gene therapy.

The present invention will be further described with reference to the following examples; however, it is to be understood that the present invention is not limited to such examples. All parts or amounts, unless otherwise specified, are by weight.

In order to facilitate understanding of the following examples, certain frequently occuring methods and/or terms will be described.

"Plasmids" are designated by a lower case preceded and/or followed by capital letters and/or numbers. The starting plasmids herein are either commercially available, publicly availabe on an unrestricted basis, or can be constructed from available plasmids in accord with published procedures. In addition, equivalent plasmids to those described are known in the art and will be apparent to the ordinarily silled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirement were used as would be known to the ordinarily skilled artisan. Fro analytical purpose, typically 1 microg of plasmid or DNA fragment is used with about 2 units of enzyme in about 20 microl of buffer solution. For the pupose of isolating DNA fragments for plasmid construction, typically 5 to 50 microg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acis Res., 8*4057 (1980 ).

"Oligonucleotides" refers to either a single stranded polydeoxynucleotide or two complementary strande polydeoxynucleotide strands which may be chemically synthesized.

Such synthetic oligonucleotides have no 5' phosphate and thus will not ligate to another oligonucleotide without adding a phosphate with an ATP in the presence of a kinas. A synthetic oligonucleotide will ligate to a fragment that has not been dephosphorylated.

"Ligation" refers to the process of forming phosphodiester bonds between two double strande nucleic acids.

Unless otherwise provided, ligation may be accomplished using known buffers and conditions with 10 units of T4 DNA ligase per 0.5 microg of approximately equimolar amounts of the DNA fragments to be ligated. Unless otherwise stated, transformation is performed as described in the methods of Graham, F. and Van Der Eb, A., Virology, 52:456–457 (1973).

EXAMPLES

Example 1

Expression and Purification of a Polypeptide of the Present Invention

The DNA sequence encoding the polypeptide of the present invention as outlined in SEQ ID NO 1 is initially amplified using PCR oligonucleotide primers corresponding to the 5' and 3' end of the DNA sequence to synthesize insertion fragments. The 5' oligonucleotide primer has the sequence of 5'-GGAATTCAGCAGCCAGGTGAGC CCAAG-3' containing an EcoRI restriction enzyme site followed by 20 nucleotides of the polypeptide coding sequence starting from the methionine start codon. The 3' primer sequence was 5'-ACTCGAGGATGCAAGC AGCAACTTTGGC-3' containing a complementary sequence to XhoI site and the last 21 nucleotides of the polypeptide coding sequence. The restriction enzyme sites correspond to the restriction enzyme sites on the pFastBac1 (Gibco BRL, Rockville, Md., U.S.A.). The plasmid vector encodes antibiotic resistance (Ampr), a bacterial origin of replication (ori), and bacterial transposon Tn7. The pFast-Bac1 vector is digested with EcoRI and XhoI and the insertion fragments are ligated into the vector maintaing the reading frame. The ligation mixture is then used to transform the E. coli strain DH10B. The transformants are selected by their ability to grow on LB plates containing Amp. Clones containing the desired construct is then transposed to Bacmid DNA by transfoming DH10 Bac with the recombinant plasmid vector containg desired heparanase gene. Transposed Bacmid DNA containing heparanase gene is selected by Blue/White selection by Bluo-gal on LB plate containg Kan, Gen, Tet, Bluo-gal, and IPTG. Clones Bacmid DNA containing desired gene is isolated, then, transfected to insect cell line Sf9 cells with CellFECTIN reagent (also available from GIBCO BRL). Harvesting of recombinant baculovirus is performed 3 days after the transfection. Expression of the polypeptide is carried out by infecting insect Tn cells with recombinant baculoviruses containing the heparanase-coding gene. Culture supernatants of infected Tn cells are collected, and heparanase is purified by affinity chromatography. Briefly, the supernatant is loaded onto a heparin-Sepharose column and then heparanase is eluted from the column by gradient solution of 0.15 to 1.0 M of NaCl.

Example 2

Assay for Identifying Agonist and Antagonist of a Polypeptide of the Present Invention For heparanase substrates, heparan sulfate labeled with fluorescein isothiocyante (FITC) is used. Briefly, 5 mg of heparan sulfate from bovine kidney (available from Seikagaku Kougyou Ltd. Tokyo, Japan) is mixed with 5 mg of FITC in 0.1 M sodium carbonate (pH 9.5), and incubated with gentle mixing at 4° C. for 12 hours. The FITC-labeled heparan sulfate is fractionated by gel filtration using a Sephacyl S-300HR column (Pharmacia Biotech, Inc.) equilibrated with 25 mM Tris-HCl, 150 mM NaCl. One to five micrograms of FITC-labeled heparan sulfate is mixed with the purified polypeptide, which is prepared as described in the example 1, in the presence or absence of agonist/antagonist and then incubated at 37° C. for 1–2 hours. The enzyme reaction is terminated by heating at 95° C. for 5 minutes. The inactivated mixture is analyzed by high-speed gel permeation chromatography using a TSKgelG3000PWXL column (available from TOSOH Ltd. Tokyo, Japan). The inhibitory activity of antagonist and the stimulatory activity of agonist are assessed by the amount of non-degraded heparan sulfate detected by a fluorescence monitor.

What is claimed is:

1. An isolated polypeptide having the amino acid sequence of amino acids 1 to 543 set forth in SEQ ID NO 2.

2. An isolated polynucleotide comprising a nucleotide sequence encoding a polypeptide as defined in claims 1.

3. An isolated polynucleotide according to claim 2 comprising the corresponding coding region contained in SEQ ID NO 1.

4. A hybrid vector comprising a polynucleotide as defined in claim 2, said polynucleotide being operably linked to suitable control sequences.

5. A hybrid vector according to claim 4, said hybrid vector being an expression vector.

6. A host cell transformed with a hybrid vector as defined in claim 5.

7. A process for the preparation of a polypeptide as defined in claim 1, said process comprising chemical synthesis, recombinant DNA technology or a combination of these methods.

8. A process for the preparation of a polypeptide said process comprising
   (i) cultivation of a host cell transformed with the hybrid vector as defined in claim 5 under conditions suitable for performing expression of the polypeptide, and
   (ii) isolation of the thus-expressed polypeptide.

9. A process for the preparation of a polynucleotide as defined in claim 2, said process comprising chemical synthesis, recombinant DNA technology, polymerase chain reaction or a combination of these methods.

10. A polypetide according to claim 1 for use in medicine.

11. A pharmaceutical composition suitable for administration to a warm-blooded organism suffering from a disease resulting from shortage or lack of a polypeptide as defined in claim 1, said composition comprising a polypeptide as defined in claim 1 together with at least one pharmaceutically acceptable carrier and/or excipient.

* * * * *

UNITED STATES PATENT AND TRADEMARK OFFICE
CERTIFICATE OF CORRECTION

PATENT NO.    : 6,461,848 B1
DATED         : October 8, 2002
INVENTOR(S)   : Nakajima et al.

It is certified that error appears in the above-identified patent and that said Letters Patent is hereby corrected as shown below:

Column 2,
Line 37, "to examine the" should read -- to the examination of --.

Column 3,
Lines 28-29, "hepatocyto" should read -- hepatocyte --.
Line 33, "laboratories(" should read -- laboratories ( --.
Line 58, "inflamed" should read -- inflamed --.
Line 62, "show a" should read -- shown that a --.
Line 67, delete "an".

Column 4,
Line 29, "one of" should read -- one of the --.
Line 30, "binds" should read -- bind --.
Line 31, "inhibits" should read -- inhibit --.
Line 35, "lead" should read -- leads --.
Line 40, "amiloid" should read -- amyloid --.
Line 57, "to polypeptide" should read -- to a polypeptide --.
Line 63, "a" (second occurrence) should be deleted.

Column 5,
Line 45, "2.I" should read -- 2. I --.

Column 6,
Line 62, "form" should read -- from --.

Column 7,
Line 62, "resideus" should read -- residues --.

UNITED STATES PATENT AND TRADEMARK OFFICE
CERTIFICATE OF CORRECTION

PATENT NO. : 6,461,848 B1
DATED : October 8, 2002
INVENTOR(S) : Nakajima et al.

It is certified that error appears in the above-identified patent and that said Letters Patent is hereby corrected as shown below:

Column 8,
Line 26, "polynucleotides" should read -- polynucleotide --.
Line 41, "vectors" should read -- vector --.
Line 46, "promotes" should read -- promoters --.
Line 49, "art" should read -- artisan --.

Column 9,
Line 22, "a s" should read -- as --.
Line 26, "fom" should read -- from --.
Line 32, "reverese" should read -- reverse --.
Line 61, "clacium phospahe" should read -- calcium phosphate --.
Line 62, "trasfection" should read -- transfection -- and "electorporation" should read -- electroporation --.

Column 10,
Line 7, "costructs" should read -- constructs --.
Line 8, "an" should read -- and --.
Line 9, "Sambrook. Et al." should read -- Sambrook et al., --.
Line 37, "imparing" should read -- purification -- and "recominant" should read -- recombinant --.
Line 38, "purificatio" should read -- purification -- and "recominant" should read -- recombinant --.
Line 46, "vetor" should read -- vector --.
Line 51, "streptomyce" should read -- Streptomyces --.
Line 62, "recombint" should read -- recombinant --.

Column 11,
Line 22, "hor" should read -- for --.
Line 34, "paricular" should read -- particular --.
Line 36, "polymorphism's" should read -- polymorphisms --.
Line 43, after "cDNA" (first occurrence) please add a period.

UNITED STATES PATENT AND TRADEMARK OFFICE
CERTIFICATE OF CORRECTION

PATENT NO.   : 6,461,848 B1
DATED        : October 8, 2002
INVENTOR(S)  : Nakajima et al.

It is certified that error appears in the above-identified patent and that said Letters Patent is hereby corrected as shown below:

Column 12,
Line 10, "positio" should read -- position --.
Line 14, "welch" should read -- Welch --.
Line 17, "physicall" should read -- physically --.
Line 32, "form" should read -- from --.
Line 34, "gened" should read -- genes --.
Line 51, "technology" should read -- technologies --.

Column 13,
Line 1, "antisense-technology" should read -- antisense technology --.
Line 18, "Therfore" should read -- Therefore --.
Line 25, "and" should read -- a --.
Line 50, "antibodie" should read -- antibody --.

Column 14,
Line 3, "inclusive" should read -- including --.
Line 4, "acitvity" should read -- activity --.
Line 7, "inclusive" should read -- including --.
Line 30, "directed to" should read -- directed to a --.
Line 61, "wate," should read -- water, --.
Line 64, "murin" should read -- murine --.
Line 65, "invation" should read -- invasion --.

Column 15,
Line 23, "of" should read -- or --; and "d the" should be deleted.
Line 41, "use medicine" should read -- use as medicine --.
Line 45, "of a polypeptide" (second occurrence) should be deleted.
Line 46, "a antibody" should read -- an antibody --.
Line 53, "inclusive" should read -- including --.

UNITED STATES PATENT AND TRADEMARK OFFICE
CERTIFICATE OF CORRECTION

PATENT NO. : 6,461,848 B1
DATED : October 8, 2002
INVENTOR(S) : Nakajima et al.

It is certified that error appears in the above-identified patent and that said Letters Patent is hereby corrected as shown below:

Column 16,
Line 1, "inclusive" should read -- including --.
Line 2, "acitvity" should read -- activity --.
Line 7, "acitvity" should read -- activity --.
Line 16, "decribed" should read -- described --.
Line 35, "silled" should read -- skilled --.
Line 41, "Fro" should read -- For --.
Line 42, "microg" should read -- microgram --.
Line 44, "microl" should read -- microliters --; and "pupose" should read -- purpose --.
Line 45, "microg" should read -- microgram --.
Line 49, "C." should read -- C --.
Line 56, "Acis" should read -- Acid --; and "8*" should read -- 8 --.
Line 58, "strande" should be deleted.
Line 63, "kinas." should read -- kinase --.
Line 67, "strande" should read -- strand --.

Column 17,
Line 3, "microg" should read -- micrograms --.
Line 33, "maintaing" should read -- maintaining --.
Line 39, "containg" should read -- containing the --.
Line 40, "containing" should read -- containing the --.

UNITED STATES PATENT AND TRADEMARK OFFICE
CERTIFICATE OF CORRECTION

PATENT NO.    : 6,461,848 B1
DATED         : October 8, 2002
INVENTOR(S)   : Nakajima et al.

It is certified that error appears in the above-identified patent and that said Letters Patent is hereby corrected as shown below:

Column 18,
Line 1, "containg" should read -- containing --.
Line 3, "containing desired" should read -- containing the desired --.
Line 25, "C." should read -- C --.
Line 30, delete "the" (first occurrence); and "example 1" should read -- Example 1 --.
Line 31, "C." should read -- C --.
Line 32, "C." should read -- C --.

Column 23,
Line 67, "claims" should read -- claim --.

Signed and Sealed this

Tenth Day of June, 2003

JAMES E. ROGAN
*Director of the United States Patent and Trademark Office*